(12) United States Patent
Brandlhuber

(10) Patent No.: US 8,712,581 B2
(45) Date of Patent: Apr. 29, 2014

(54) SAMPLE ANALYSIS AND/OR SAMPLE PROCESSING SYSTEM

(76) Inventor: Martin Brandlhuber, St. Wolfgang (DE)

( * ) Notice: Subject to any disclaimer, the term of this patent is extended or adjusted under 35 U.S.C. 154(b) by 461 days.

(21) Appl. No.: 13/041,931

(22) Filed: Mar. 7, 2011

(65) Prior Publication Data

US 2011/0231015 A1    Sep. 22, 2011

(30) Foreign Application Priority Data

Mar. 19, 2010  (DE) .......................... 10 2010 016 029

(51) Int. Cl.
*G06F 7/00* (2006.01)

(52) U.S. Cl.
USPC .......................................... 700/229; 700/214

(58) Field of Classification Search
USPC .......................................... 700/214, 228, 229
See application file for complete search history.

(56) References Cited

U.S. PATENT DOCUMENTS

| 5,172,690 A | 12/1992 | Berthier | |
| 6,256,553 B1 * | 7/2001 | Erikkila | 700/213 |
| 7,783,383 B2 * | 8/2010 | Eliuk et al. | 700/245 |
| 7,930,066 B2 * | 4/2011 | Eliuk et al. | 700/245 |
| 8,423,174 B2 * | 4/2013 | Koch et al. | 700/214 |
| 2004/0134750 A1 * | 7/2004 | Luoma, II | 198/340 |
| 2008/0190735 A1 * | 8/2008 | Luoma | 198/340 |

FOREIGN PATENT DOCUMENTS

GB    2 260 974 A    5/1993

OTHER PUBLICATIONS

German Search Report for DE 10 2010 016 029.6.

* cited by examiner

*Primary Examiner* — Ramya Burgess
(74) *Attorney, Agent, or Firm* — Renner Kenner Greive Bobak Taylor & Weber

(57) ABSTRACT

A sample analysis and/or sample processing system having a robotic system includes at least one carrier in which one or more objects are retained, a positioning region having a plurality of defined Positions for positioning the at least one carrier, a robot for approaching the object(s) in the carrier, and a control unit for storing the position of the carrier and the objects retained therein and for controlling the robot. The positioning region has an elongate profile-member having a plurality of coupling positions stored in the control unit, and the carrier provides a coupling for suspending the carrier in a specific coupling position on the elongate profile-member.

12 Claims, 4 Drawing Sheets

Figure 1:
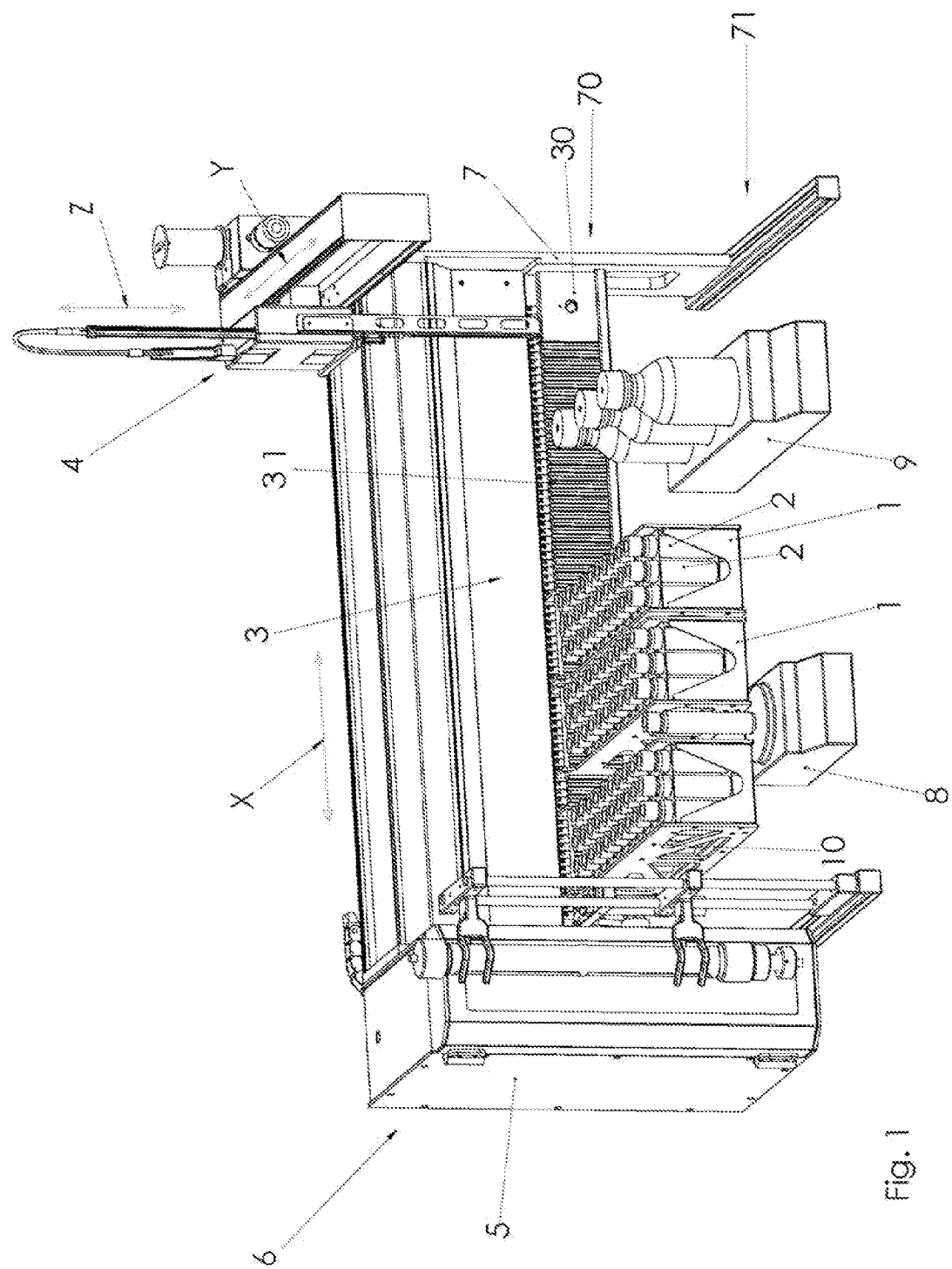

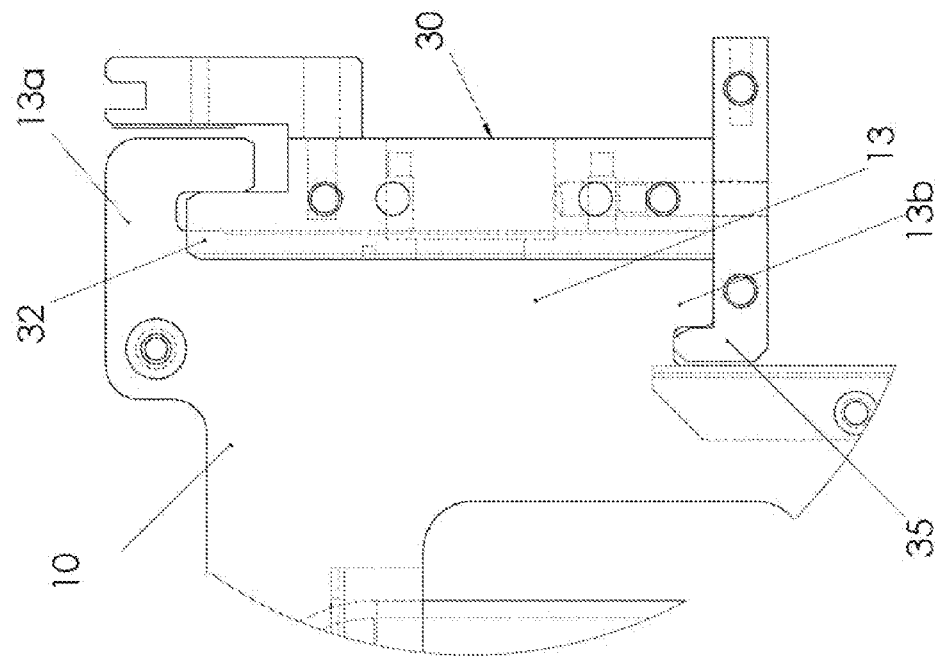
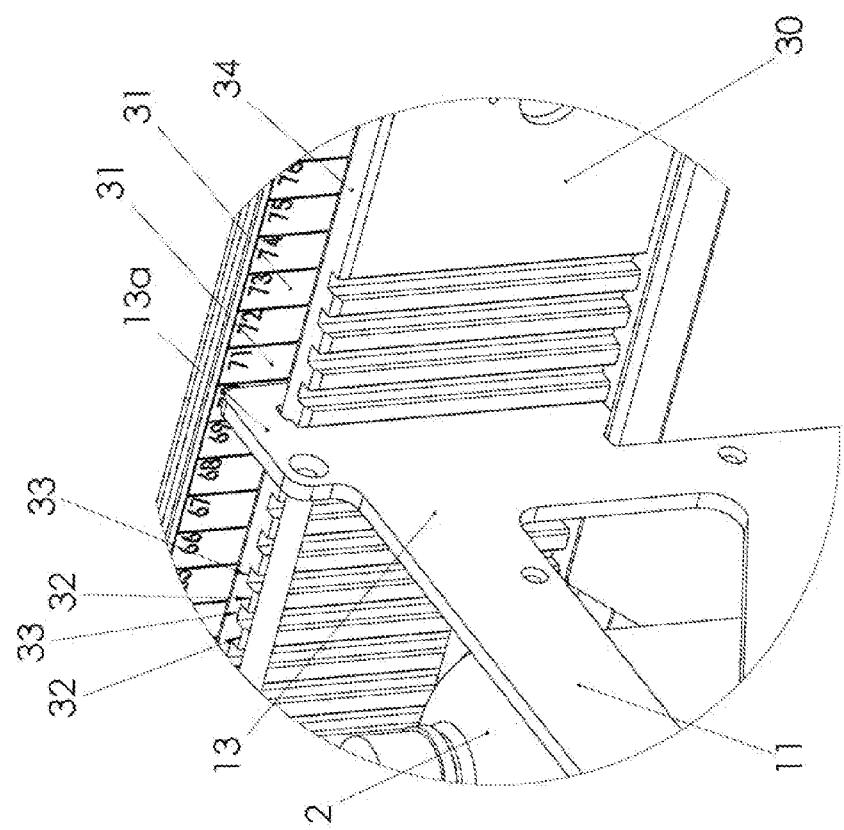
Fig. 4
Fig. 3

SAMPLE ANALYSIS AND/OR SAMPLE PROCESSING SYSTEM

This application claims priority from German Patent Application No. 10 2010 016 029.6 filed on Mar. 19, 2010, which is incorporated herein by reference in its entirety.

The invention relates to a sample analysis and/or sample processing system having a robotic system, the robotic system having at least one carrier, in which one or more objects are retained, and a robot for approaching the objects in the carrier.

Robotic systems are used, for example, for the fully automated analysis and/or processing of samples. To this end, a plurality of carriers, each having a plurality of objects, are generally arranged in one level, the individual samples being approached by the robot in order, for example, to move parts of the samples to that location for processing or analysis purposes. The samples are, for example, liquid or solid materials which are stored in a container.

In a system which is known in practice, the carriers are secured beside each other on a rail. In another system the carriers are placed on a platform, the carriers being able to be locked in predetermined positions. In order to initialise the robotic system, the individual carriers are approached with the robot in order to store the precise position of the carriers or the objects thereof in the system. However, these known systems are not suitable for carrying out constantly changing operations, which require changed carrier positions and/or objects.

DE 689 08 634 T2 further discloses a method and a device for controlling stackers. GB 2 260 974 A describes an automatic system for retrieving selected items of clothing which are placed on hangers.

An object of the invention was to provide a sample analysis and/or sample processing system with a robotic system which allows very flexible combination and positioning of the carriers with objects which are the same or different.

This object is achieved according to the invention by the features of claim 1.

The sample analysis and/or sample processing system according to the invention has a robotic system having substantially the following components:
a. at least one carrier in which one or more objects are retained,
b. a positioning region having a plurality of defined positions for positioning the at least one carrier,
c. a robot for approaching the object(s) in the carrier and
d. a control unit for storing the position of the carrier and the objects which are retained therein and for controlling the robot.

The positioning region has an elongate profile-member having a plurality of coupling positions which are stored in the control unit and the carrier provides coupling means for suspending the carrier in a specific coupling position on the elongate profile-member.

The carriers are consequently simply suspended at a desired coupling position. Since every conceivable coupling position is already stored in the control unit, the system must only know the position at which the carrier was suspended. This can be implemented, for example, by all coupling positions being provided with corresponding markings, for example, figures, so that it is necessary only to enter which type of carrier is involved and at which coupling position it is suspended.

In the context of the invention, however, it is also conceivable for the carrier to be provided with a corresponding marking, a transmitter or the like in order to enable automatic identification and location of the carriers. To this end, it is possible to use, for example, an RFID system.

The samples to be analysed or processed are, for example, liquid or solid materials which are stored in a container or mixtures of materials as found, for example, in the analysis of foodstuffs, animal feed, the environment and pharmaceuticals.

The subsidiary claims relate to other configurations of the invention.

The robot and preferably also the elongate profile-member can be retained on a frame.

According to a preferred configuration, the coupling means of the carrier have at least a first suspension hook which is suspended on the elongate profile-member. The coupling means may further have at least a second suspension hook or pin which co-operates with a receiving region of the elongate profile-member that is constructed accordingly in a complementary manner. This receiving region may be formed, for example, by a hook-like bar which protrudes in the direction of the carrier and which extends over the length of the elongate profile-member and in which the second suspension hook or pin engages. In the preferred configuration, the elongate profile-member has a plurality of webs which are arranged in a comb-like manner, there being formed between the webs intermediate spaces in which the coupling means of the carrier are received in a play-free manner when the carrier is in the suspended state. The webs which are arranged in a comb-like manner can be provided at the side facing or the side remote from the at least one suspended carrier.

It is further advantageous for the elongate profile-member to be orientated in a horizontal manner and for the elongate profile-member and the coupling means of the carrier to be constructed in such a manner that the carrier, when suspended in the vertical direction, is lowered into the desired coupling position. Preferably, the coupling means are formed by a first and a second coupling means which are constructed in an identical manner and which, when the carrier is in the suspended state, are arranged on the carrier in the longitudinal direction of the elongate profile-member with spacing from each other. In this manner, it is possible to achieve very stable and play-free retention of the carriers. According to a specific configuration of the invention, the carrier is constructed in a box-like manner with a first and a second lateral boundary wall, the two lateral boundary walls being orientated perpendicularly relative to the longitudinal extent of the elongate profile-member when the carrier is in the suspended state and the first coupling means being formed by the end of the first boundary wall facing the elongate profile-member and the second coupling means being formed by the end of the second boundary wall facing the elongate profile-member.

The robot can be moved in a conventional manner in the x, y and z direction. In order to increase the operating range of the robot, at least two operating levels are preferably provided, the elongate profile-member being arranged and orientated in such a manner that the suspended carriers are located in the first operating level and the second operating level is formed below the suspended carriers. It is thus possible to arrange, for example, in the lower second operating level, a scale, a heating and/or a stirring device.

Figure 2:
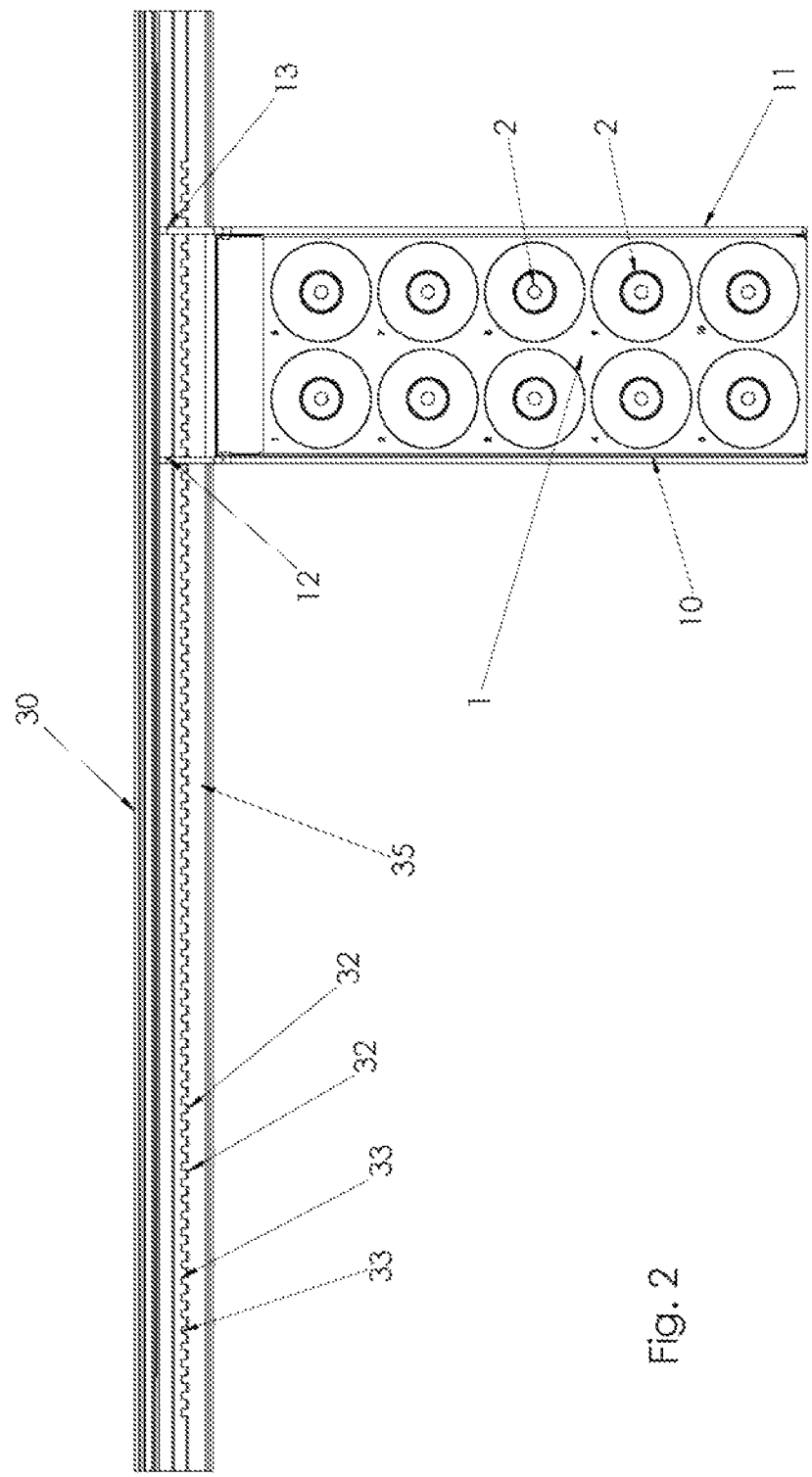
Figure 5:
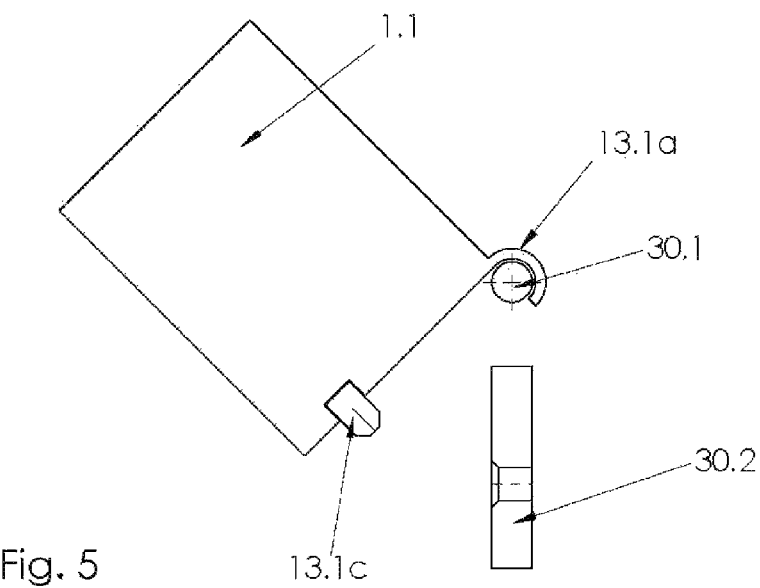
Figure 6:
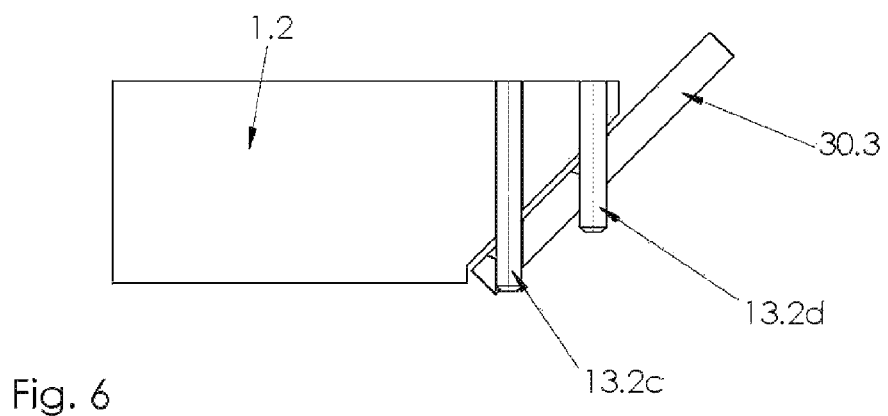
Figure 7:
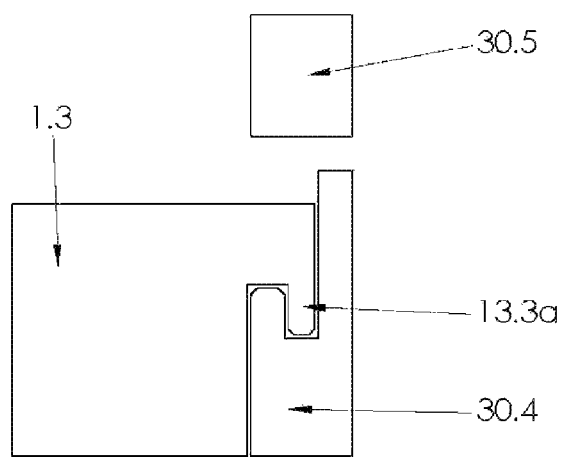

Other advantages and configurations of the invention will be explained in greater detail below with reference to the description and the drawings, in which:

FIG. 1 is a three-dimensional illustration of the robotic system according to the invention, FIG. 2 is a plan view in the positioning region, FIG. 3 is a three-dimensional detailed view in the region of the connection between the carrier and elongate profile-member, FIG. 4 is a side view of the detailed view according to FIG. 3, FIG. 5 is a schematic side view of a carrier and an elongate profile-member according to a second embodiment, FIG. 6 is a schematic side view of a carrier and an elongate profile-member according to a third embodiment, and FIG. 7 is a schematic side view of a carrier and an elongate profile-member according to a fourth embodiment.

FIG. 1 illustrates a sample analysis and/or sample processing system having a robotic system, the robotic system substantially having the following components:

- a plurality of carriers 1, in which one or more objects 2 are retained,
- a positioning region 3 having a plurality of defined positions for positioning the carriers 1,
- a robot 4 for approaching the object(s) in the carriers 1, and
- a control unit 6 which is accommodated in a switch box 5 for storing the positions of the carriers 1 and the objects 2 which are retained therein and for controlling the robot 4.

The positioning region 3 has an elongate profile-member 30 having a plurality of coupling positions 31 which are stored in the control unit 6. The profile-member 30 which is constructed in a rail-like manner is retained horizontally on a frame 7 in such a manner that the carriers 1 can be suspended on the elongate profile-member 30 in specific coupling positions. The robot 4 which is also retained on the frame 7 can be moved in the x, y and z direction. Depending on the application, it is provided with an appropriate tool, for example, a pipette needle. The range of the robot 4 is adapted to the suspended carriers 1 in such a manner that it can approach each of the objects 2 retained in the carriers 1.

The carriers 1 which are suspended on the elongate profile-member 30 are located in a first operating level 70 which is raised with respect to the support surface of the frame 7 so that a second operating level 71 is formed below the suspended carriers 1. This second operating level 71 which is, for example, the support surface of the entire robotic system, is used, for example, to position a scale 8 or a device 9 for stirring or heating.

The devices arranged in the second operating level are advantageously positioned in such a manner that they are not concealed by the carrier 1 in order to ensure the accessibility for the robot 4.

With reference to FIGS. 2 to 4, the securing of the carriers 1 to the elongate profile-member 30 is explained in greater detail below.

The elongate profile-member has a plurality of webs 32 which are arranged in a comb-like manner, intermediate spaces 33 being formed between the webs. As can also be seen from FIG. 1, the carriers 1 are constructed in a box-like manner with a first and a second lateral boundary wall 10, 11. The ends of the boundary walls 10, 11 facing the elongate profile-member 30 when the carriers 1 are in the suspended state are constructed as first and second coupling means 12, 13. They are constructed in an identical manner and are described below in greater detail with reference to FIGS. 3 and 4 with respect to the coupling means 13.

The coupling means 13 is provided with a first suspension hook 13a and a second suspension hook 13b and the elongate profile-member 30 has an upper front edge 34 which the carrier 1 engages around with the first suspension hook of the coupling means 12, 13. At the same time, a portion of the coupling means 12, that is to say, the front edge of the boundary wall 13 is received in a play-free manner in one of the intermediate spaces 33 of the elongate profile-member 30. The second suspension hook 13b of the coupling means 13 co-operates with a receiving region 35 of the profile-member 30 that is constructed accordingly in a complementary manner. In the embodiment illustrated, the receiving region 35 is formed by a hook-like bar which protrudes in the direction of the carrier 1 and which extends over the length of the profile-member 30 and in which the second suspension hook 13b engages as can be seen in particular from FIG. 4.

The elongate profile-member 30 is orientated in a horizontal manner, the coupling means 12, 13 of the carriers 1 being constructed in such a manner that the carrier is lowered into the desired coupling position when suspended in a vertical direction. Owing to a correspondingly precisely fitting construction of the suspension hooks 13a, 13b and the intermediate spaces 33, the carriers are suspended in a very stable and play-free manner. The stability is also increased by the two coupling means 12, 13 being arranged on the carrier in the longitudinal direction of the elongate profile-member 30 with spacing from each other.

As can be seen from FIG. 3, the various coupling positions are inscribed with sequential numbers. The coupling means 13 of the carrier is thus suspended at the coupling position "70".

The positioning region 3 described above consequently allows the carriers 1 to be fitted to the elongate profile-member 30 without any tools, the carriers being able to be suspended at a plurality of different coupling positions 31.

Depending on the application, various types of carriers can be used with objects which are the same or different. In the control unit 6, all possible carrier types and all coupling positions are advantageously stored. If the robotic system is reconfigured, the control unit 6 must consequently merely be informed as to which type of carrier is suspended at which coupling position. Owing to the type of carrier, it is known to the system how many objects are provided in the carrier and where the objects 2 are located in the carrier, so that the robot can approach the objects in a precise manner. The inputting is carried out via a keyboard which is not illustrated in greater detail and a screen, the type of carrier and also the coupling positions advantageously being able to be selected from a menu.

However, instead of manually inputting the type of carrier and coupling position, this can also be carried out in a fully automated manner, for example, by the carriers being provided with an RFID system which co-operate with corresponding sensors at the various coupling positions. It is also conceivable for the type of carriers and the coupling positions to be evaluated and determined using a camera and image processing.

Although the positioning region described with reference to FIGS. 2 to 4 constitutes a preferred embodiment, other configurations are also possible in the context of the invention. Some of these variants are illustrated in FIGS. 5 to 7.

In the embodiment according to FIG. 5, the elongate profile-member is formed by a rod 30.1 and a perforated bar 30.2, the carrier 1.1 having a first suspension hook 13.1a which comes into engagement with the rod 30.1. In order to prevent horizontal displacement of the carriers 1.1 along the rod 30.1, the carrier 1.1 additionally has pins 13.1c which co-operate with the perforated bar 30.2.

In the embodiment according to FIG. 6, the elongate profile-member 30.3 is arranged in an inclined manner and the carriers 1.2 have coupling means which are constructed accordingly in an inclined manner and which are provided with pins 13.2c and 13.2b which engage in corresponding recesses of the elongate profile-member 30.3.

Another embodiment is illustrated in FIG. 7 in which the suspension hook 13.3a of the carrier 1.3 does not engage around an upper front edge of the elongate profile-member but is instead suspended in a corresponding recess of a 1- or 2-part profile-member 30.4/30.5.

In all the embodiments, extremely flexible combination and positioning of the carriers with different objects is enabled. Owing to the suspension or the hanging of the carriers, the region below the carriers is free and can be kept clean in a simple manner or can be used for an additional operating level. The positioning region described above also allows the carriers to be freely combined and replaced in an extremely rapid and simple manner.

The invention claimed is:

1. Sample analysis and/or sample processing system comprising:
   a. at least one carrier in which one or more objects are retained,
   b. a positioning region having a plurality of defined positions for positioning the at least one carrier,
   c. a robot for approaching the one or more objects in the carrier and
   d. a control unit for storing the position of the carrier and the position of the one or more objects retained therein and for controlling the robot, characterised in that the positioning region has an elongate profile-member having a plurality of coupling positions which are stored in the control unit and the carrier provides coupling means for suspending the carrier in a specific coupling position on the elongate profile-member.

2. Sample analysis and/or sample processing system according to claim 1, characterised in that the robot is retained on a frame.

3. Sample analysis and/or sample processing system according to claim 1, characterised in that the elongate profile-member is retained on a frame.

4. Sample analysis and/or sample processing system according to claim 1, characterised in that the coupling means of the carrier have at least a first suspension hook which is suspended on the elongate profile-member.

5. Sample analysis and/or sample processing system according to claim 4, characterised in that the coupling means of the carrier have at least a second suspension hook or pin which co-operates with a receiving region of the elongate profile-member that is constructed accordingly in a complementary manner.

6. Sample analysis and/or sample processing system according to claim 5, characterised in that the receiving region of the elongate profile-member is formed by a hook bar which protrudes in the direction of the carrier and which extends over the length of the elongate profile-member and in which the second suspension hook or pin engages.

7. Sample analysis and/or sample processing system according to claim 1, characterised in that the elongate profile-member has a plurality of webs which are arranged in a comb manner, there being formed between the webs intermediate spaces in which the coupling means of the carrier are received in a play-free manner when the carrier is in the suspended state.

8. Sample analysis and/or sample processing system according to claim 7, characterised in that the webs which are arranged in a comb manner are provided at the side facing or the side remote from the at least one suspended carrier.

9. Sample analysis and/or sample processing system according to claim 1, characterised in that the elongate profile-member is orientated in a horizontal manner and the elongate profile-member and the coupling means of the carrier are constructed in such a manner that the carrier, when suspended in the vertical direction, is lowered into the desired coupling position.

10. Sample analysis and/or sample processing system according to claim 1, characterised in that the coupling means are formed by a first and a second coupling means which are constructed in an identical manner and which, when the carrier is in the suspended state, are arranged on the carrier in the longitudinal direction of the elongate profile-member with spacing from each other.

11. Sample analysis and/or sample processing system according to claim 10, characterised in that the carrier is constructed in a box-like manner with a first and a second lateral boundary wall, the two lateral boundary walls being orientated perpendicularly relative to the longitudinal extent of the elongate profile-member when the carrier is in the suspended state and the first coupling means being formed by the end of the first boundary wall facing the elongate profile-member and the second coupling means being formed by the end of the second boundary wall facing the elongate profile-member.

12. Sample analysis and/or sample processing system according to claim 1, characterised in that at least two operating levels are provided, the elongate profile-member being arranged and orientated in such a manner that the suspended carriers are located in the first operating level and the second operating level is formed below the suspended carriers.

* * * * *